(12) United States Patent
Krcma

(10) Patent No.: US 7,764,186 B2
(45) Date of Patent: Jul. 27, 2010

(54) GAS SENSING METHOD AND INSTRUMENT THEREFOR

(75) Inventor: Jan Krcma, Valparaiso, IN (US)

(73) Assignee: J And N Enterprises Inc., Valparaiso, IN (US)

( * ) Notice: Subject to any disclaimer, the term of this patent is extended or adjusted under 35 U.S.C. 154(b) by 297 days.

(21) Appl. No.: 12/107,445

(22) Filed: Apr. 22, 2008

(65) Prior Publication Data
US 2008/0258926 A1    Oct. 23, 2008

Related U.S. Application Data

(60) Provisional application No. 60/913,305, filed on Apr. 23, 2007.

(51) Int. Cl.
*G08B 17/10* (2006.01)
(52) U.S. Cl. ...................................... 340/632; 73/31.06
(58) Field of Classification Search ................. 340/632, 340/511, 692; 73/23.2, 31.05, 31.06; 330/1 R, 330/1 A, 3
See application file for complete search history.

(56) References Cited

U.S. PATENT DOCUMENTS

| | | | | |
|---|---|---|---|---|
| 3,864,628 A | * | 2/1975 | Klass et al. | 73/31.06 |
| 4,198,621 A | * | 4/1980 | Roper | 340/870.39 |
| 4,399,684 A | * | 8/1983 | Advani et al. | 73/31.06 |
| 4,441,024 A | * | 4/1984 | Anderson | 250/380 |
| 4,510,792 A | * | 4/1985 | Morel et al. | 73/40.7 |
| 5,742,200 A | * | 4/1998 | He | 329/320 |
| 6,467,334 B2 | * | 10/2002 | Lloyd et al. | 73/31.06 |
| 6,960,770 B2 | * | 11/2005 | Klaas | 250/343 |
| 7,268,609 B2 | | 9/2007 | van Staveren et al. | |
| 7,304,741 B2 | | 12/2007 | Sadeghi et al. | |
| 2002/0168772 A1 | * | 11/2002 | Lloyd et al. | 436/37 |

OTHER PUBLICATIONS

B. Licznerski, Thick-film gas microsensors based on tin dioxide, vol. 52, No. 1, 2004, Bulletin of the Polish Academy of Sciences Technical Sciences.
Figaro an ISO9001 company, technical information for TGS2611, Revised Apr. 2002.

* cited by examiner

*Primary Examiner*—John A Tweel, Jr.
(74) *Attorney, Agent, or Firm*—Hartman & Hartman, P.C.; Gary M. Hartman; Domenica N.S. Hartman

(57) ABSTRACT

A method and instrument capable of accurately detecting the presence of a gas and accurately measuring the concentration of the gas in, for example, the environment. The method and instrument sense the presence of a gas with a sensing element whose output is linear to the concentration of the gas in the environment, and process the output of the sensing element through a nonlinear amplifier having a higher gain at lower levels of the output than at higher levels of the output so that the nonlinear amplifier amplifies the output of the sensing element at the lower levels thereof and avoids signal saturation at the higher levels thereof. The method and instrument then deliver the amplified output of the nonlinear amplifier to an audio circuit that produces an audio output having a property in proportion to the amplified output of the nonlinear amplifier.

20 Claims, 2 Drawing Sheets

GAS SENSING METHOD AND INSTRUMENT THEREFOR

CROSS REFERENCE TO RELATED APPLICATIONS

This application claims the benefit of U.S. Provisional Application No. 60/913,305, filed Apr. 23, 2007, the contents of which are incorporated herein by reference.

BACKGROUND OF THE INVENTION

The present invention generally relates to devices and methods for detecting and/or measuring substances. More particularly, this invention relates to a gas sensing method and instrument capable of detecting the presence of a gas at low levels within an environment, and accurately measuring the concentration of the gas in the environment.

Gas leak detectors are widely used in the mining industry and by utility company personnel, first responders, and others to detect the presence of potentially harmful or dangerous gases, a notable but nonlimiting example being hydrocarbon gases such as methane. Gas leak detectors typically use a thick-film metal oxide semiconductor sensor whose metal oxide film is reactive to the targeted gas and when reacted exhibits a change (usually a drop) in electrical resistance. The response is nonlinear relative to the amount of targeted gas present, and as such typical gas leak detectors are very sensitive at low level concentrations (e.g., up to about 10,000 ppm), but lose their sensitivity at higher concentrations (generally at a few percentages of gas concentration) at which point the output is said to encounter signal saturation. An example is the FIGARO 2600 series methane gas sensor model TGS2611, commercially available from Figaro Engineering Inc.

FIG. 1 represents by example a gas detector 10 that utilizes a nonlinear sensor 12 of the type described above. The sensor 12 is interfaced with audio circuitry 20 containing an audio device 24 for producing an audible "tick" whose rate or frequency is in proportion to the gas concentration sensed by the sensor 12. As used herein, an "audible tick" refers to a variable repetition rate of audio pulses, each, for example, approximately 250 msec in duration, to which a human ear is very responsive. The tick rate alerts the user to the presence of a gas to which the sensor 12 is sensitive and, prior to the onset of signal saturation, the relative amount of gas. As evident from FIG. 1, the sensor 12 interfaces with the circuitry 20 by functioning as part of a resistive (voltage) divider circuit that contains the sensor 12 and a resistor 14 connected in series to a suitable DC or AC voltage source 16. The resistive divider circuit is shown connected to a linear amplifier 22, the audio device 24, and a speaker 26 (or other audible sound-generating device), which cooperate to convert voltage to an audible sound. The audio device 24 is represented as a voltage controlled oscillator (VCO)/pulse generator, whose repetition rate is in proportion to gas concentration sensed by the sensor 12 and drives the speaker 26. Gas detector circuits of the type represented in FIG. 1, including its circuit components and their electrical properties, are well known in the art and therefore will not be discussed in any further detail here. The electrical values of the components are indicated in FIG. 1 for reference purposes only.

Because of their nonlinear response characteristics, semiconductor-type gas sensors are not well suited for performing actual measurements of gas concentrations. In contrast, pellistors and other types of sensors, e.g., infrared (IR) sensors, are more suitable for actual measurement of gas concentration because they have essentially linear responses. As well known in the art, the detecting element within a pellistor comprises catalyst-loaded pellets or beads of a ceramic material whose resistance changes with temperature. The catalyst is usually a palladium and/or platinum alloy, which oxidizes organic gas molecules to yield largely water vapor and carbon dioxide. The resulting change in temperature from the heat of oxidation causes a change in resistance in the ceramic material, which in turn is then measured and related to the quantity of the targeted gas present in the environment or other sample. An example of a pellistor sensor is the model CH-D3 combustible gas pellistor commercially available from Alphasense Ltd. Because their output response is linear, pellistor-type sensors are not ideally suited for use as leak detectors requiring high sensitivity at very low gas concentrations (e.g., below a few percentages of gas concentration).

In view of the above issues, combinations of nonlinear sensors and linear sensors are widely used when the desire is to provide a device capable of both gas detection and gas concentration measurement. However, it would be desirable to avoid the cost of combining both technologies in a single instrument.

BRIEF SUMMARY OF THE INVENTION

The present invention provides a method and instrument capable of accurately detecting the presence of a gas and accurately measuring the concentration of the gas in, for example, the environment.

According to a first aspect of the invention, the method includes sensing the presence of a gas with a sensing element whose output is linear to the concentration of the gas in the environment, processing the output of the sensing element through a nonlinear amplifier having a higher gain at lower levels of the output than at higher levels of the output so that the nonlinear amplifier amplifies the output of the sensing element at the lower levels thereof and avoids signal saturation at the higher levels thereof, and then delivering the amplified output of the nonlinear amplifier to an audio circuit that produces an audio output having a property in proportion to the amplified output of the nonlinear amplifier.

According to a second aspect of the invention, the instrument includes a sensing means comprising a sensing element whose output is linear to the concentration of the gas in the environment, processing means comprising a nonlinear amplifier that amplifies the output of the sensing element, and an audio circuit to which the amplified output of the nonlinear amplifier is delivered. The nonlinear amplifier has a higher gain at lower levels of the output than at higher levels of the output, and thereby amplifies the output of the sensing element at the lower levels thereof and avoids signal saturation at the higher levels thereof. The audio circuit produces an audio output having a property in proportion to the amplified output of the nonlinear amplifier.

In view of the above, it can be seen that a significant advantage of this invention is that the method and instrument do not require combinations of linear and nonlinear sensing elements to provide both gas detection and gas concentration measurement capabilities over a broad range of gas concentrations. Instead, the method and instrument make use of a linear sensing element in combination with a nonlinear amplifier whose high gain at low output levels achieves heightened sensitivity at low output signal levels of the linear sensing element to provide a desirable gas detection capability (e.g., targeted gas levels below one percent), and whose lower gain at higher output levels of the linear sensing element maintains the capability for gas concentration measurement associated with the linear sensing element (preferably targeted gas levels approaching 100%).

Other objects and advantages of this invention will be better appreciated from the following detailed description.

DETAILED DESCRIPTION OF THE INVENTION

Figure 1:
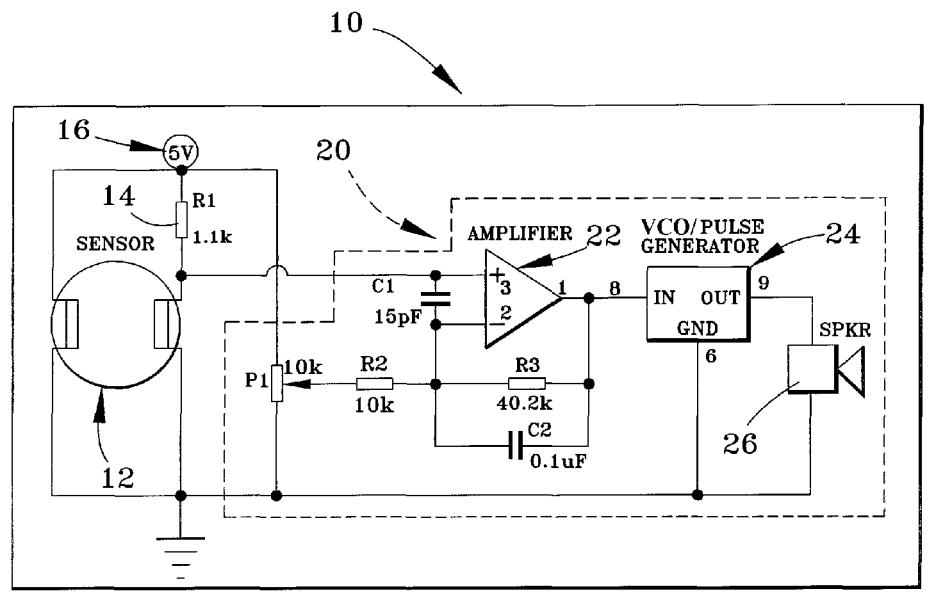
FIG. 1 is a schematic representation of circuitry for a gas detector in accordance with the prior art.
Figure 2:
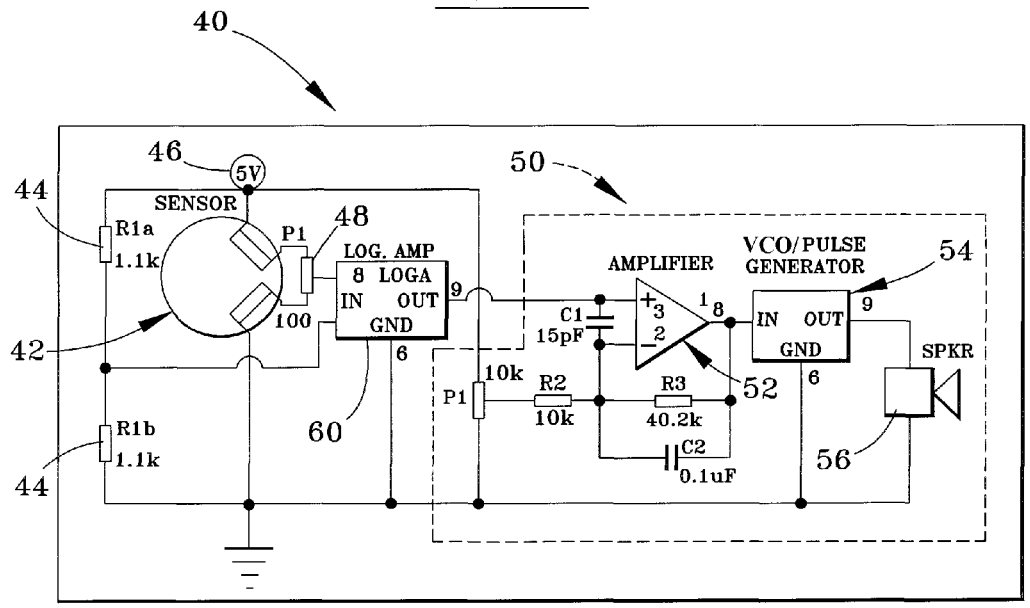
FIG. 2 is a schematic representation of circuitry for a gas sensing instrument in accordance with a first embodiment of this invention.
Figure 3:
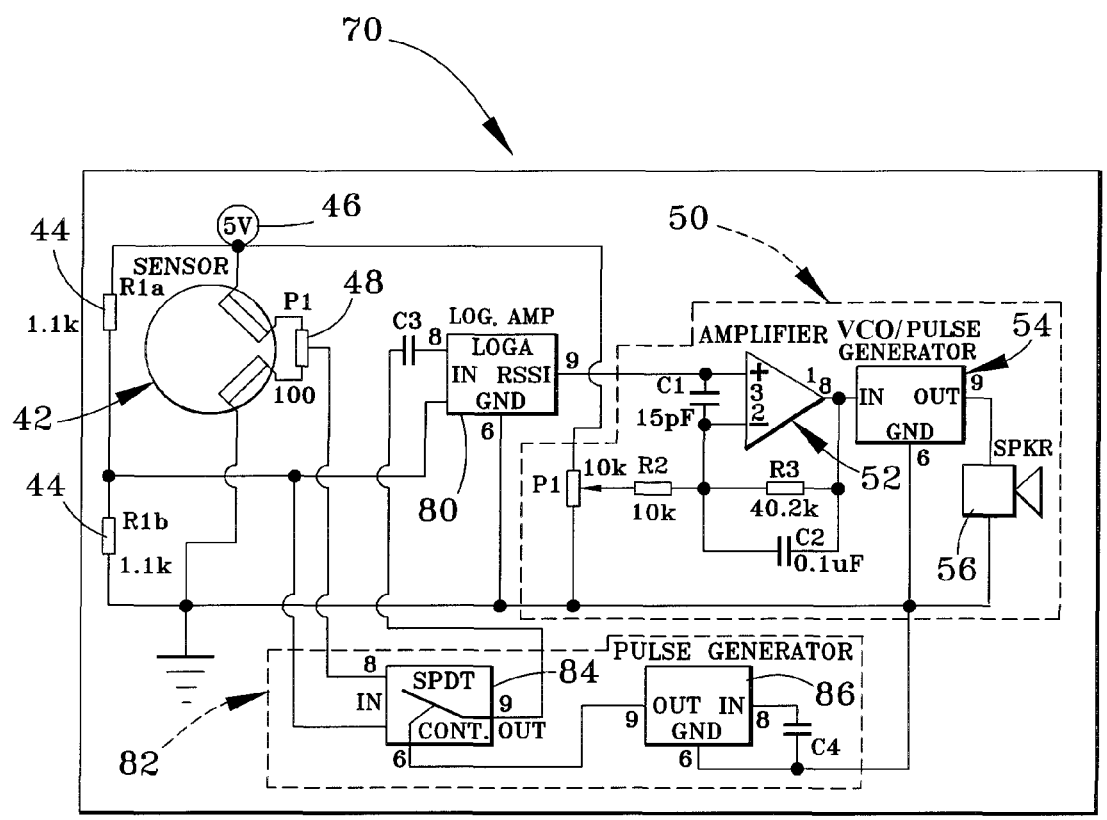
FIG. 3 is a schematic representation of circuitry for a gas sensing instrument in accordance with a second embodiment of this invention.

FIGS. 2 and 3 depict circuitries for two embodiments of gas sensing instruments within the scope of this invention. As will become evident from the following discussion, the circuitries make use of an essentially linear sensing element to enable the instruments to perform very accurate gas concentration measurements. The instruments further include interface circuitries that enable the linear sensing elements to also be used as very sensitive gas detectors capable of matching or exceeding the performance of commonly-used nonlinear sensors employed by prior art gas detection instruments (e.g., FIG. 1). The circuit components represented in FIGS. 2 and 3 are well known in the art and therefore will not be discussed in any detail here. Electrical values of these components are indicated in FIGS. 2 and 3 for reference purposes only, and are not to be interpreted as limiting the scope of the invention.

In FIG. 2, a circuit 40 is represented as including a pellistor 42 connected with resistors 44 in a bridge circuit powered by a suitable DC or AC voltage source 46. As known in the art, the pellistor 42 contains a catalyst-loaded ceramic material whose resistance changes or can be made to change in the presence of the targeted gas, for example, helium, hydrogen, carbon monoxide (CO), hydrogen sulfide ($H_2S$), or hydrocarbon gases including but not limited to natural gas and/or one of its constituents, such as methane, ethane, propane, butane, and/or pentane. An example of a suitable catalytic pellistor is the model CH-D3 combustible gas pellistor commercially available from Alphasense Ltd. This type of pellistor operates in combination with a heater (not shown) that burns the targeted gas; the generated heat produces a change in the electrical resistance of the catalyst-loaded ceramic material in proportion to the gas concentration. While a pellistor 42 is shown and believed to be preferred, other linear sensing elements could be employed by the circuit 40, examples of which include thermal conductivity sensors (TC), infrared sensors (IR), electrochemical sensors, semi-conductor sensors, MEMS, corona, and tunable laser diode spectroscopy, all of which are well known in the art.

Balance adjustments to the bridge circuit are shown as being made possible with a variable resistor 48 through a mechanical interface such as, for example, a potentiometer or a microprocessor addressable device. The output of the bridge circuit may by amplified by an optional amplifier (not shown) to bring the output signal of the pellistor 42 to a level suitable for further processing. The output signal of the pellistor 42 is then fed to a dc-coupled nonlinear (e.g., logarithmic) amplifier 60 (or other nonlinear amplification device). The nonlinear amplifier 60 is chosen to have a high gain at low signal levels and a progressively decreasing gain at higher signal levels. For example, a suitable logarithmic amplifier 60 is AD8307 available from Analog Devices, and has a relatively high gain of about 80 dB at a voltage of about 100 µV, and a lower gain of about 0 dB at a voltage of about 500 mV. The gain of the amplifier 60 preferably decreases logarithmically over the entire output range of the pellistor 42.

In view of the above, the circuit 40 is able to employ the pellistor 42 in a manner that advantageously utilizes the linearity of the pellistor 42 to accurately measure gas concentrations at high levels (e.g., gas concentrations approaching 100%), while also exhibiting high sensitivity at very low gas concentrations (e.g., gas concentrations below 1%). As such, a gas detecting instrument equipped with the circuit 40 can exhibit a gas detection capability similar to that of nonlinear thick-film metal oxide detectors, while avoiding the signal saturation condition that renders nonlinear detectors unsuitable for performing gas concentration measurements at high gas concentrations.

FIG. 2 further represents the circuit 40 as containing audio circuitry 50 that includes, for example, an audio amplifier or microprocessor-based device that converts voltage to sound that is audible to a human. As with the prior art instrument of FIG. 1, the audio circuitry 50 is represented as containing a linear amplifier 52 and audio device (VCO/pulse generator) 54 that generates a pulsed output whose pulse rate is in proportion to the gas concentration sensed by the pellistor 42. The output of the pulse generator 54 drives the speaker 56, which produces an audible "tick" whose rate or frequency is in proportion to the output of the pellistor 42, which in turn is in proportion to the gas concentration sensed by the pellistor 42. As such, the tick rate can be used to alert the user to the presence of the gas to which the pellistor 42 is sensitive. While a tick rate is preferred for providing an audible indication of gas concentration, other audible signals are possible and within the scope of this invention.

Aside from the descriptions provided above, the circuit 40, its circuit components, and their electrical properties do not require any further detailed discussion here. Exemplary electrical values for the circuit components are indicated in FIG. 2 for reference purposes only.

A lower-cost alternative to the use of the dc-coupled nonlinear amplifier 60 represented in FIG. 2 is to use an ac-coupled amplifier. Such an embodiment is represented in FIG. 3, which shows an ac-coupled logarithmic amplifier 80 in combination with a chopper circuit 82. In FIG. 3, the chopper circuit 82 is represented by a single-pull double-throw switch 84 and a pulse generator 86, though functional alternatives well-known to those skilled in the art are also within the scope of the invention. The amplifier 80 can be a common ac logarithmic amplifier, for example, an FM limiting amplifier with an RSSI (received signal strength indication) output signal. As well known in the art, the chopper circuit 82 serves to break up the output signal of the pellistor 42 delivered to the amplifier 80, so that the output signal can be processed by the amplifier 80 as if it were an AC signal. The output (e.g., RSSI) signal of the amplifier 80 then emulates the response of a nonlinear-type sensing element (e.g., FIG. 1). Particularly suitable ac-coupled logarithmic amplifiers typically have an approximately 60 to 80 dB (1000 to 10,000:1) dynamic range, with only a few dB departure from a logarithmic law.

Aside from the inclusion of the ac-coupled logarithmic amplifier 80 and chopper circuit 82, the circuit 70 of FIG. 3 can share the same electrical components as the circuit 40 of FIG. 2, and as such FIG. 3 uses consistent reference numbers to identify such functionally similar components.

From the above, it should be appreciated that the circuits 40 and 70 represented in FIGS. 2 and 3 provide relatively inexpensive instruments capable of detecting the presence of a gas at low levels, combined with accurate gas concentration level measurements at much higher levels. Each circuit 40 and 70 is believed to be capable of implementation at a fraction of the cost of including a secondary nonlinear sensing device. As represented in FIGS. 2 and 3, the circuits 40 and 70 also provide the capability of interfacing with audio devices 54 to generate an audible output, preferably a "tick" rate in some relation to the gas concentration sensed by the pellistor 42, such that the user is not only alerted to the presence of a gas to which the pellistor 42 is sensitive, but also the concentration of the gas over a much broader range than possible with nonlinear sensors of the prior art (e.g., FIG. 1).

While the invention has been described in terms of specific embodiments, it is apparent that other forms could be adopted by one skilled in the art. For example, the physical configurations of the circuits 40 and 70 and their components could differ from that shown, and yet achieve the intended operation obtained by combining a linear sensing element and a nonlinear amplifier to detect and measure gas levels. Therefore, the scope of the invention is to be limited only by the following claims.

The invention claimed is:

1. A method for detecting the presence of a gas and measuring the concentration of the gas in an environment, the method comprising the steps of:
   sensing the presence of the gas with a sensing element whose output is linear to the concentration of the gas in the environment;
   processing the output of the sensing element through a nonlinear amplifier having a higher gain at lower levels of the output than at higher levels of the output, the nonlinear amplifier thereby amplifying the output of the sensing element at the lower levels thereof and avoiding signal saturation at the higher levels thereof; and then
   delivering the amplified output of the nonlinear amplifier to an audio circuit that produces an audio output having a property in proportion to the amplified output of the nonlinear amplifier.

2. The method according to claim 1, wherein the sensing element is a pellistor.

3. The method according to claim 1, wherein the nonlinear amplifier is a dc-coupled logarithmic amplifier.

4. The method according to claim 1, wherein the nonlinear amplifier is an ac-coupled logarithmic amplifier.

5. The method according to claim 4, further comprising a chopper circuit between the sensing element and the ac-coupled logarithmic amplifier.

6. The method according to claim 1, wherein the audio circuit produces an audible tick having a frequency in proportion to the amplified output of the nonlinear amplifier.

7. The method according to claim 1, wherein the audio circuit does not receive an output derived from a sensing element whose output is nonlinear to the concentration of the gas in the environment.

8. The method according to claim 1, wherein the gas is a chosen from the group consisting of hydrocarbons, helium, hydrogen, carbon monoxide, and hydrogen sulfide.

9. The method according to claim 1, wherein the gas is a hydrocarbon.

10. An instrument for detecting the presence of a gas and measuring the concentration of the gas in an environment, the instrument comprising:
    means for sensing the presence of the gas, the sensing means comprising a sensing element whose output is linear to the concentration of the gas in the environment;
    means for processing the output of the sensing element, the processing means comprising a nonlinear amplifier having a higher gain at lower levels of the output than at higher levels of the output, the nonlinear amplifier thereby amplifying the output of the sensing element at the lower levels thereof and avoiding signal saturation at the higher levels thereof; and
    an audio circuit to which the amplified output of the nonlinear amplifier is delivered, the audio circuit producing an audio output having a property in proportion to the amplified output of the nonlinear amplifier.

11. The instrument according to claim 10, wherein the sensing element is a pellistor.

12. The instrument according to claim 10, wherein the nonlinear amplifier is a dc-coupled logarithmic amplifier.

13. The instrument according to claim 10, wherein the nonlinear amplifier is an ac-coupled logarithmic amplifier.

14. The instrument according to claim 3, further comprising a chopper circuit between the sensing element and the ac-coupled logarithmic amplifier.

15. The instrument according to claim 1, wherein the audio circuit is operable to produce an audible tick having a frequency in proportion to the amplified output of the nonlinear amplifier.

16. The instrument according to claim 1, wherein the audio circuit does not receive an output derived from a sensing element whose output is nonlinear to the concentration of the gas in the environment.

17. The instrument according to claim 1, wherein the sensing element contains a catalyst-loaded ceramic material whose resistance changes in the presence of a gas.

18. The instrument according to claim 1, wherein the sensing element contains a catalyst-loaded ceramic material whose resistance changes in the presence of a gas chosen from the group consisting of hydrocarbons, helium, hydrogen, carbon monoxide, and hydrogen sulfide.

19. The instrument according to claim 1, wherein the sensing element contains a catalyst-loaded ceramic material whose resistance changes in the presence of a hydrocarbon gas.

20. The instrument according to claim 1, wherein the sensing element is a component of a bridge circuit that further comprises a variable resistor adapted to make balance adjustments to the bridge circuit.

* * * * *